US005712282A

United States Patent [19]
Iyo et al.

[11] Patent Number: 5,712,282
[45] Date of Patent: Jan. 27, 1998

[54] METHOD FOR THERAPEUTICALLY TREATING TARDIVE DYSKINESIA AND USES THEREOF

[75] Inventors: Masaomi Iyo, 21-15 Makuharihongo, Chiba; Hajime Sasaki, Funabashi; Yohko Maeda, Ichinomiya; Kenji Hashimoto, Kadaira; Toshiya Inada, Ichikawa; Yoshie Kitao, Tokyo, all of Japan

[73] Assignees: Masaomi Iyo, Chiba; Meiji Seika Kaisha, Ltd., Tokyo, both of Japan

[21] Appl. No.: 727,654

[22] PCT Filed: Apr. 14, 1995

[86] PCT No.: PCT/JP95/00736

§ 371 Date: Oct. 9, 1996

§ 102(e) Date: Oct. 9, 1996

[87] PCT Pub. No.: WO95/28177

PCT Pub. Date: Oct. 26, 1995

[30] Foreign Application Priority Data

Apr. 15, 1994 [JP] Japan ................................ 6-077146

[51] Int. Cl.$^6$ .................... A61K 31/52; A61K 31/415; A61K 31/40
[52] U.S. Cl. .................... 514/263; 514/392; 514/424
[58] Field of Search .................... 514/424, 263, 514/392

[56] References Cited

PUBLICATIONS

Budavari, Ed., The Merck Index, Eleventh Edition pp. 1312–1313, entry No. 8235 1989.

*Primary Examiner*—William R.A. Jarvis
*Attorney, Agent, or Firm*—Larson & Taylor

[57] ABSTRACT

A method for therapeutically treating tardive dyskinesia, which comprises a compound having an enzyme-inhibitory activity against a phospho-diesterase as the active ingredient, is now provided. Rolipram is preferred as the active ingredient. When rolipram is administered to such rats as experimental model, which have tardive dyskinesia induced by consecutive administrations of haloperidol, there can be obtained such curative effect that the symptoms of tardive dyskinesia are suppressed dose-dependently.

5 Claims, No Drawings

METHOD FOR THERAPEUTICALLY TREATING TARDIVE DYSKINESIA AND USES THEREOF

This application is a 371 of PCT/JP95/00736, filed Apr. 14, 1995.

TECHNICAL FIELD

This invention relates to a new pharmaceutical composition for therapeutically treating tardive dyskinesia, which comprises a compound having an enzyme-inhibitory activity against enzymatic functions of phosphodiesterases as an active ingredient, and this invention also relates to uses of said composition.

BACKGROUND ART

Tardive dyskinesia is a disease which is accompanied with chronic and involuntary movements appearing in the face, head or trunk of the patients which are incurred in association with long-term administration of various drugs, mainly such antipsychotic drugs, especially a curative drug for schizophrenia, that act as an antagonist to dopamine $D_2$ receptors of the dopamine neuron system in the corpus striatum of the brain. The time of occurrence of said involuntary movements is found at a time of from several months to several years lapsed from the starting of the administration of the above antipsychotic drugs. In some case, said disease can occur even when the dosage of said antipsychotic drug had been reduced or when the administration of the drug had been withdrawn. This disease can often continue for a long time even when the withdrawal of the administration of the antipsychotic drugs had been made. Some portions of the involuntary movements may often be irreversible, namely be refractory.

For example, haloperidol is a compound of butyrophenone-type and is such a representative drug for treating schizophrenia, which acts as the antagonist against the dopamine $D_2$ receptors present in the dopamine neuron system in the corpus striatum of the brain. Haloperiodol has been used extensively in the clinics for nearly 40 years. However, it is well known that a long-term administration of haloperidol brings about induction of tardive dyskinesia as an adverse reaction.

The above-mentioned involuntarily occurring abnormal movements of tradive dyskinesia appear mainly in the muscles around the mouth and appear also in the facial muscles, particularly the muscles of cheeks, tongue and jaws and are characterized by mumble-like movements, but these involuntary movements can sometime appear also in the head, trunk and limbs. Tardive dyskinesia is neurologically classified as a hyper-activity of extra-pyramidal system in central motor pathway which is connecting to the spinal motor neuron, and tardive dyskinesia is thought to be attributable to a defficiency of the inhibitory mechanism in corpus striatum of the brain. Problems to be solved in clinical practice for this disease are such that the abnormal movements of tardive dyskinesia would continue even after the withdrawal of the medication with the antipsychotic drugs and eventually become chronic and ultimately become refractory (see Inada T, K. Ohnishi, M. Kamisada, G. Matsuda, O. Tajima, Y. Yanagisawa, K. Hashiguchi, S. Shima, Y. Oh-e, Y. Masuda, T Chiba, K. Kamijima, R. W. Rockhold and G. Yagi, "A prospective study of tardive dyskinesia in Japan", Psychiat. Clin. Neurosci., 240, pp. 250–254 (1991)). However, any curative drugs which are sufficiently effective to tardive dyskinesia have not been discovered yet so far. In case tardive dyskinesia has occurred, there is no alternative but to withdraw the administration of the antipsychotic drugs to the patients or to reduce the dosage of these drugs. These methods of withdrawing the administration of the antipsychotic drugs or of reducing the dosage of these drugs can bring about an aggravation or recurrence of the initial psychosis and hence cannot necessarily provide a really effective measure for treating the patients. Accordingly, it is now demanded for a long time to provide a curative drug which is effective and useful to therapeutically treat tardive dyskinesia.

A hypothesis has been presented to suppose that, in case of the occurrence of tardive dyskinesia which is induced by a long-term administration of the antipsychotic drugs, the dopamine $D_2$ receptors present in the dopamine neuron system of the corpus striatum in the brain or the function of the dopamine $D_2$ receptors would have involved a supersensitivity thereof. However, any experimental results which can be useful to demonstrate and support the aforesaid hypothesis has not yet been obtained before (see Waddington, J. L., "Spontaneous orofacial movements induced in rodents by very long-term neuroleptic drug administration: phenomenology, pathology and putative relationship to tardive dyskinesia", Psychopharmachology, 101, pp. 431–447(1990)). When such a medicine for Parkinson's disease, which is usually used in the therapy of acute symptoms of the extrapyramidal system in the central motor pathway, is administered to the patients upon the occurrence of tardive dyskinesia, it is actually observed that the symptoms of tardive dyskinesia can rather be aggravated. Besides, it is often observed that when once tardive dyskinesia has occurred, the symptoms of this disease are aggravated transitorily even if the administration of the antipsychotic drug has been stopped, and that after the stoppage of administration of the antipsychotic drug, a long time is required to obtain a reduction in the symptoms of tardive dyskinesia or that the symptoms of this disease can become irreversible.

On the other hand, it is known that the above-mentioned dopamine $D_2$ receptors inhibit the activity of adenylate cyclase (AC) via the function of the inhibitory guanosine-5'-triphosphate (GTP)-binding protein (Gi), resulting in suppressing the conversion of ATP (adenosine triphosphate) into cAMP (cyclic adenosine-3',5'-monophosphate). Thus, the dopamine $D_2$ receptors do affect the second messenger system and regulate the physiological activities of the neuron.

Furthermore, a phosphodiesterase (abbreviated as PDE) is an enzyme which hydrolyzes a cyclic nucleotide such as cAMP or the like. It is known that PDE includes at least five sub-types of PDE (PDE I, II, III, IV and V) which are differentiated from each other in view of the factors of controlling the enzymatic activity of PDE and in view of the substrate specificities of PDE. It is known that PDE I, PDE II and PDE III can hydrolyze cAMP and cGMP (cyclic guanosine-3',5'-monophosphate) to an approximately same extent (non-specifically), that PDE IV has a high specificity to cAMP and that PDE V has a high specificity to cGMP.

Meanwhile, it is also known that rolipram (namely, ($\pm$)-4-[3-(cyclopentyloxy)-4-methoxyphenyl]-2-pyrrolidinone) is one of such compounds which inhibit the enzymatic activity of PDE, that is, PDE inhibitors, and that rolipram is effective as antidementia drug for demensia which is incurred by disturbances in the brain blood vessels (see the specifications of U.S. Pat. No. 5,059,612; European patent application publication No. 0 432 856; and Japanese patent application publication "Kokai" No. Hei-3-181418). It is further known that when an inhibitor to the PDE which hydrolyzes cAMP can have penetrated into the brain, the level of cAMP in the brain is increased thereby (see, Schneider et al.; "Brain cAMP response to phosphodiesterase inhibitors in rats killed by microwave irradiation or decapitation", Biochem. Pharmacol. Vol. 33, pp. 1690–1693 (1984)).

Incidentally, there has not been reported hithertobefore any hypothesis which supposes that a decrease in the cAMP level in the corpus striatum of the brain or a decrease in the cAMP level in the brain would have important attribution in the mechanism of the occurrence of tardive dyskinesia. And, there has not been reported any investigation which is directed to studying the decrease in the cAMP levels as mentioned above, in a relationship to tardive dyskinesia.

DISCLOSURE OF THE INVENTION

We, the present inventors, have made many investigations in an attempt to provide and exploit such medicines which are effective for therapeutic treatment of tardive dyskinesia. On the basis of the results accumulated from such our investigations, the present inventors have now been able to confirmatively recognize such a conclusion that tardive dyskinesia is incurred with being attributable to a super-sensitivity of the dopamine $D_2$ receptors which has been involved under the influence of the long-term administration of an antipsychotic drug acting as an antagonist to the dopamine $D_2$ receptors. Thus, the present inventors have now obtained such assumption that the amount of cAMP being produced from ATP via the action of AC in the brain cells of the patients with the occurrence of tardive dyskinesia has been decreased very much extra-ordinarily via the function of Gi by the action of the intrinsic dopamine, and that the extraordinary decrease of cAMP may elicit the symptoms of dyskinesia (the involuntary movements).

Therefore, the present inventors have now obtained such an expectation that the symptoms of dyskinesia can be ameliorated if the extraordinarily progressed decrease in the amount of the cAMP in the brain can be suppressively controlled.

As described hereinbefore, a phosphodiesterase (PDE) is the enzyme which hydrolyzes cyclic nucleotides such as cAMP etc. As described hereinbefore, it is also known that such a compound having the activity to inhibit the PDE's enzymatic activity of hydrolyzing cAMP (said compound is hereinafter sometime referred to simply as PDE inhibitor) is able to increase the levels of cAMP in the brain when the PDE inhibitor can have penetrated into the brain. With taking into account that the physiological action of the PDE inhibitor is not dependent on the receptors for neurotransmittors, the present inventors can have obtained further an expectation such that even in the states of the super-sensitivity of the dopamine $D_2$ receptors, administration of the PDE inhibitor may also ameliorate such super-sensitivity of the dopamine $D_2$ receptors in a direction toward their state of normality at the stage of the second neurotransmission, if administration of the PDE inhibitor is effective. From the above reasons, the present inventors firstly have now presumed that such a PDE inhibitor, particularly a PDE IV inhibitor, which has an ability to penetrate the blood-brain barrier, may potentially be effective as a drug for therapeutically treating tardive dyskinesia.

On the basis of the above expectations and presumptions now obtained by the present inventors, the present inventors have conducted such tests wherein rolipram (its chemical name: (±)-4-[3-(cyclopentyloxy)-4-methoxyphenyl]-2-pyrrolidinone) having a selective inhibitory activity to PDE IV (cAMP-specific PDE), as well as several kinds of the other PDE inhibitors are used and administered to rats as the experimental model in which tardive dyskinesia has been induced experimentally by a long-term administration of haloperidol in the rats, for the purpose of the therapeutic treatment of tardive dyskinesia. Thus, the present inventors firstly have succeeded in finding confirmatively that these PDE inhibitors tested are practically effective to therapeutically treat and remedy tardive dyskinesia. The present inventors have now found further that in general, such a compound having an enzyme-inhibitory activity against a cAMP-hydrolyzing phosphodiesterase is useful and effective to therapeutically treat and remedy tardive dyskinesia which has been incurred by a long-term administration of an antipsychotic drug, especially a curative drug for schizophrenia, which acts as an antagonist to the dopamine $D_2$ receptor in the dopamine neuron system in the brain.

Futhermore, the present inventors have now found that the compound having the inhibitory activity against PDE can be formulated into a pharmaceutical composition for therapeutic treatment of tardive dyskinesia by admixing said compound with a pharmaceutically acceptable solid or liquid carrier which is conventional in the pharmaceutics, and that generally, said compound can be administered via an oral or parenteral route to a patient in need of the therapeutic treatment of tardive dyskinesia.

According to a first aspect of this invention, therefore, there is provided a pharmaceutical composition for therapeutically treating tardive dyskinesia, characterized in that said composition comprises a compound which has an enzyme-inhibitory activity against a phosphodiesterase and is able to penetrate the blood-brain barrier after administration of said compound, as an active ingredient, in association with a pharmaceutically acceptable carrier for the active ingredient.

BEST EMBODIMENTS FOR THE INVENTION

A pharmaceutical composition according to the first aspect of this invention may preferably contain as the active ingredient such a compound which has the enzyme-inhibitory activity against phosphodiesterase IV, namely a phosphodiesterase active specifically to cyclic adenosine-3', 5'-monophosphate (cAMP) and which is able to penetrate the blood-brain barrier after administration of said compound, and which may be rolipram, for example.

The compound having the inhibitory activity against PDE, which may be used as the active ingredient in the above-mentioned pharmaceutical composition of this invention, includes the aforesaid Rolipram, as well as Propentofylline ("Merck Index", 11th-edition, Code No. 7823; Chemical name: 3,7-dihydro-3-methyl-1-(5-oxohexyl)-7-propyl-1H-purine-2,6-dione), Denbufylline (Chemical name: 7-(2-oxopropyl)-1,3-di-n-butylxanthine), Ro 20-1724 [Journal of Medicinal Chemistry, Vo. 34, No. 1, page 293 (1991)], Theofylline ("Merck Index", 11th-edition, Code No. 9212; Chemical name: 3,7-dihydro-1,3-dimethyl-1H-purine-2,6-dione), Vinpocetine ("Merck Index", 11th-edition, Code No. 9894; Chemical name: eburnamenine 14-carboxylic acid ethyl ester), and IBMX (Chemical name: 3-isobutyl-1-methylxanthine), or the like.

The pharmaceutical composition of this invention comprising the above-mentioned compound as the active ingredient may be formulated into various forms of the preparation by admixing the active ingredient compound with a solid or liquid carrier which is conventionally employed in the pharmaceutics.

Such values of the concentration of the above exemplified compounds having the DPE-inhibiting activity and usable as the active ingredient in the pharmaceutical composition of this invention, at which said compounds can inhibit in vitro the enzymatic activity of a phosphodiesterase by 50%, that is, the $IC_{50}$ values of said compounds to PDE are disclosed in some literatures already published, and such $IC_{50}$ values are shown in the following Table 1 along with the names of the literatures.

TABLE 1

| Common name of compound | $IC_{50}$ value (μM) to phosphodiesterase | Type of PDE to be inhibited | Referential Literature (see Notes) |
|---|---|---|---|
| Rolipram | 1 | IV | a |
| Propentofylline | 81 ~ 246 | | b |
| Denbufylline | 0.3 | IV | c |
| Ro 20-1724 | 2 | IV | a |
| Theophylline | ~200 | I ~ V | a |
| Vinpocetine | 20 | I | a |
| IBMX | 2 ~ 50 | I ~ V | a |

Notes: Names of Referential Literatures:
a: Trend in Pharmacological Science (TiPS), Vol. 11, pp. 150–155 (April, 1990)
b: Arzneim. -Forsch./Drug Res. 35 (II), p. 1034 (1985)
c: Journal of Biological Chemistry, Vol. 267, p. 1798, (January, 1992)

The compound having the PDE-inhibiting activity and usable as the active ingredient in the pharmaceutical composition of this invention for therapeutic treatment of tardive dyskinesia may preferably be such a PDE inhibitor that can exhibit the activity preferentially inhibitory to the enzymatic activity of a phosphodiesterase which is present in the brain of mammals and is active specifically to cAMP, for example, the phosphodiesterase IV. The strength of the phosphodiesterase-inhibiting activity of the compounds which have the activity inhibitory to PDE and are usable as the active ingredient in accordance with this invention may generally be assayed in vitro by any standard methods for the determination of the enzyme-inhibitory activities of enzyme inhibitors.

Moreover, as assumed that it is reasonable for the present inventors to presume that tardive dyskinesia can occur due to the extraordinarily progressed decrease in the level of cAMP present in the brain cells as stated hereinbefore, it is expected that in case the occurrence of tardive dyskinesia is foreseen from the long-term administration of the antipsychotic drug, tardive dyskinesia may be prevented from occurring by preliminary administration of the compound having the phosphodiesterase-inhibiting activity usable according to this invention to the patient prior to a coming occurrence of tardive dyskinesia so that an extraordinarily progressed decrease in the level of cAMP in the brain cells is reduced or inhibited in advance.

Upon oral administrations, the dosage of the pharmaceutical composition according to the first aspect of this invention may be in a range of 0.001 to 1000 mg in terms of the active ingredient compound per day for one adult. The pharmaceutical composition containing the active ingredient compound having the PDE-inhibiting activity according to this invention may be formulated into various preparations by the procedures conventional in the technical field of pharmaceutics. The forms of the preparations for oral administration are not limited particularly, and may usually be, for example, tablets, granules, powders, capsules and the like. More particularly, the active ingredient compound according to this invention may be formulated into such preparations by admixing said compound with excipient, if necessary, along with binder, disintegrator, lubricant, colorant or others, followed by shaping the resultant admixture into tablets, coated tablets, granules, powders, capsules or the like as desired, in a conventional manner. Further, for the parenteral or non-oral administration, the pharmaceutical composition of this invention may be administered in the form of a solution containing the active ingredient compound dissolved therein or in the form of a suspension containing the active ingredient compound dispersed therein.

In more details, the active ingredient compound having the PDE-inhibiting activity usable according to this invention may be administered in the form of a pharmaceutical composition which has been formulated into injectable preparations or oral preparations or the like, where said compound is mixed and associated with the excipient or carrier. The excipient or carrier may be chosen from the pharmaceutically acceptable ones, and the nature and composition of the excipient or carrier may vary dependently on the route of administration and the method of administration of the pharmaceutical composition as formulated. For instance, as a liquid carrier, there may be used water, alcohols, or animal or vegetable oils or synthetic oils, including soybean oil, mineral oil, sesami oil and the like. As a solid carrier, there may be used sugars such as maltose and sucrose, etc., amino acids such as lysine etc., cellulose derivatives such as hydroxypropylcellulose etc., polysaccharides such as cyclodextrins etc., and salts of organic acids such as magnesium stearate, and the like. When the composition of this invention is formulated into an injectable preparation, the liquid carrier used may generally be a physiological saline, various kinds of buffered solutions, solutions of a sugar such as glucose, inositol and mannitol, and glycols such as ethylene glycol and polyethylene glycol, and the like. Further, the composition of this invention may also be formulated into a lyophilized injectable preparation, in association with one or more excipients which may be a sugar such as inositol, mannitol, glucose, mannose, maltose and sucrose, as well as an amino acid such as phenylalanine. Upon the administration, the lyophilized injectable preparation may be used after it has been dissolved or suspended in a solvent suitable for the injection, for example, sterilized water, physiological saline, aqueous solution of glucose, aqueous solution of electrolytes and an intravenously injectable solution of amino acids. Then, an appropriate surface-active agent may be added into said preparation for use as a solubilizing agent to assist the active ingredient compound to be dissolved in the solvent used.

The content of the active ingredient present in the pharmaceutical composition as formulated may vary dependently on the form of the formulated composition but usually may be in a range of 0.001 to 99% by weight, preferably of 0.01 to 90% by weight based on the total weight of the composition. For instance, it is preferable that an injectable solution contains the active ingredient compound in a proportion of 0.01 to 5% by weight. For the oral administration, the active ingredient compound may be used by formulating it into a form such as tablet, capsule, powder, granule, dried syrup, liquor, syrup or the like, in association with a solid carrier or a liquid carrier as mentioned above. In the capsule, tablet, granule or powder, the proportion of the active ingredient compound therein may usually be in a range of 0.01 to 99% by weight, preferably of 0.02 to 90% by weight, with the balance being the carrier.

The dosage of the active ingredient used according to this invention may generally be determined with taking account of the age, body weight, symptoms of the patient and the therapeutic purpose as intended. However, this active ingredient can be administered continuously or intermittently as long as its total dosage does not exceed a specific level that was decided in view of the results of animal tests and various circumstances for the patient. Optimal dosage of the active ingredient and the number of the administration of the active compound under definite conditions can be decided by expert doctors. Furthermore, in a second aspect of this invention, there is provided a method for therapeutically treating tardive dyskinesia, which comprises administering a therapeutically effective amount of a compound which has an enzyme-inhibitory activity against a phosphodiesterase, specially phosphodiesterase IV and is able to penetrate the blood-brain barrier after administration of said compound, to a patient in need of the treatment and having received occurrence of tardive dyskinesia as induced by long-term administration of such an antipsychotic drug, particularly a curative drug for schizophrenia, which acts as an antagonist against the dopamine $D_2$ receptor in the dopamine neuron system in the brain.

Moreover, in another aspect of this invention, this invention embraces a use of such a compound which has an enzyme-inhibitory activity against a phosphodiesterase and is able to penetrate the blood-brain barrier after administration of said compound, in the manufacture of a drug for therapeutically treating tardive dyskinesia.

In a further another aspect of this invention, there is further provided a process for the manufacture of a pharmaceutical composition for therapeutically treating tardive dyskinesia, which comprises admixing a compound having an enzyme-inhibitory activity against a phosphodiesterase and being able to penetrate the blood-brain barrier after administration of said compound, with a pharmaceutically acceptable solid or liquid carrier.

A preferred example of the compound which may preferably be used as the active ingredient in accordance with this invention is rolipram. It is known that rolipram is a selective inhibitor against a phosphodiesterase which is active specifically to cAMP, and that rolipram can increase the concentration of cAMP in the brain of rats as shown by the animal tests (Journal of Medicinal Chemistry, Vol. 34, No. 1, pp. 291–293 (1991)).

In the following, there are shown some examples of the results of tests where acute toxicity of rolipram in rats was measured.

| Route of administration | $LD_{50}$ value |
|---|---|
| Intraperitoneal | about 500 mg/kg |
| Oral | about 1200 mg/kg |

Below are described Test Examples in which tardive dyskinesia in the experimental model of rats was therapeutically treated by intraperitoneal administration of rolipram used as the active ingredient according to this invention.

Test Example 1

Haloperidol was intraperitoneally administered to each rat of SD-strain rats (male, 6 rats per group) at a dose of 1.5 mg/kg once a day for consecutive three weeks. After lapse of 96 hours from the completion of the last administration of haloperidol, the number of the vacuous chewing movements of the mouth and the number of abnormal tongue-protruding movements of the rats were counted as the parameters indicative of tardive dyskinesia.

Rolipram was formulated into the form of a suspension in which rolipram was partially dissolved and partially dispersed in a vehicle composed of a physiological saline containing 10% by weight of Cremophor (a surface active agent). To the rats under test was administered intraperitoneally the test compound, namely rolipram in the form of said suspension at doses of 0.5 mg/kg and 1.0 mg/kg. After the lapse of 3 minutes from the administration of rolipram, the rats were observed for 15 minutes, and the numbers of the above-mentioned abnormal movements appearing for the observation period of 15 minutes were counted, in comparison with the number of the abnormal movements appearing in the control group of rats to which only the vehicle composed of the physiological saline containing 10% Cremophor was administered. Then, values of the numbers of said abnormal movements (Mean±Standard error) were calculated, and the results obtained are shown in Table 2 below.

TABLE 2

| Test groups of rats treated with test compound | Number of the chewings | Number of the tongue protrusions |
|---|---|---|
| Control group (treated with Vehicle only) | 111.2 ± 27.8 | 7.7 ± 2.1 |
| Group treated with Rolipram (0.5 mg/kg) | 32.2 ± 14.5 | 2.7 ± 1.7 |
| Group treated with Rolipram (1.0 mg/kg) | 8.8 ± 4.0 | 1.5 ± 1.5 |

It is observed that rolipram administered both at the doses of 0.5 mg/kg and 1.0 mg/kg exhibited such therapeutic effect that rolipram suppresses in a dose-dependent manner the symptoms of tardive dyskinesia in the experimental rat model having the disease induced by the consecutive administrations of haloperidol in the rats.

Test Example 2

Haloperidol decanoate was intramuscularly injected in the femoral region of each rat of SD-strain rats (male, 6 rats per group) at a dose of 25 mg/kg once for every 4 weeks during the total period of 24 weeks.

Rolipram or IBMX was formulated into the form of a suspension in which said compound was partially dissolved and partially dispersed in a physiological saline containing 10% Cremophor. After lapse of 8 weeks from the final administration of haloperidol decanoate, rolipram or IBMX in the form of said suspension was intraperitoneally administerd at different doses into the rats under test. To the control group of rats was intraperitoneally administered only the physiological saline containing 10% Cremophor.

After the lapse of 15 minutes from the administration of the test compound, the rats were observed for 15 minutes. The numbers of the vacuous chewing movements and the abnormal tongue-protruding movements appearing during the 15 min. period of the observation were counted as indices of oral dyskinesia in the rats.

Values of Mean±Standard error of the numbers of the abnormal movements as observed were calculated, and the results obtained are shown in Table 3 below. Rolipram was found to suppress in a dose-dependent manner the oral dyskinesia which had been induced by the long-term administration of haloperidol decanoate in the rats. It is also found that the administration of IBMX had a tendency to suppress the above-mentioned oral dyskinesia.

TABLE 3

| Test groups of rats treated with test compound | Number of the Chewings | Number of the tongue protrusions |
|---|---|---|
| Control group (treated with Vehicle only) | 213.3 ± 50.5 | 17.2 ± 5.5 |

TABLE 3-continued

| Test groups of rats treated with test compound | Number of the Chewings | Number of the tongue protrusions |
| --- | --- | --- |
| Group treated with 0.1 mg/kg of rolipram | 138.0 ± 38.1 | 6.0 ± 2.2 |
| Group treated with 0.5 mg/kg of rolipram | 33.8 ± 13.8 | 1.7 ± 1.1 |
| Group treated with 1.0 mg/kg of rolipram | 42.0 ± 9.5 | 1.3 ± 1.1 |
| Group treated with 2.0 mg/kg of IBMX | 135.3 ± 45.0 | 4.8 ± 1.8 |

Test Example 3

Haloperidol in the form of a suspension of haloperidol in 0.5% aqueous carboxymethylcellulose was intraperitoneally administrated at a dose of 1.5 mg/kg to each rat of SD-strain rats (female, 7 to 8 rats per group) once a day for consecutive five weeks.

Ro 20-1724 was formulated into the form of a suspension in which said compound was partially dissolved and partially dispersed in a physiological saline containing 10% Cremophor. On the next day of the final administration of haloperidol, Ro 20-1724 as the suspension was intraperitoneally administered at a dose of 3 mg/kg, 10 gm/kg or 30 mg/kg in the rats under test. To the control group of rats was administered only the physiological saline containing 10% Cremophor.

After the lapse of 15 minutes from the administration of the test compound, each rat under test was observed for totally 15 minutes. The numbers of the vacuous chewing movements and the abnormal tongue-protruding movements appearing during the 15 min. period of the observation were counted as the indices of oral dyskinesia in the rats. The net observation time was calculated by substracting from the total observation time of 15 minutes the amount of time which the rat spent in exploration or grooming. The indices of the oral dyskinesia were expressed as the number of occurrence of the abnormal movements observed in one minute of the net observation time.

Values of the numbers of the abnormal movements (Mean±Standard error) were thus evaluated, and these results are shown in Table 4 below. It is found that Ro 20-1724 suppressed in a dose dependent manner the oral dyskinesia induced by the repeated administrations of haloperidol in rats.

TABLE 4

| Test groups of rats treated with test compound (n: number of rats per group) | Number of the chewings | Number of the tongue protrusions |
| --- | --- | --- |
| Control group (treated with Vehicle only) (n = 7) | 16.2 ± 2.4 | 1.90 ± 0.87 |
| Groups treated with 3 mg/kg of Ro 20-1724 (n = 8) | 11.7 ± 2.1 | 0.46 ± 0.17 |
| Groups treated with 10 mg/kg of Ro 20-1724 (n = 8) | 3.5 ± 1.0 | 0.10 ± 0.07 |
| Groups treated with 30 mg/kg of Ro 20-1724 (n = 8) | 2.9 ± 0.7 | 0.04 ± 0.04 |

Example 1 for Preparation 0.05 Parts by weight of rolipram, 55 parts by weight of lactose, 45 parts by weight of crystalline cellulose, 0.3 parts by weight of magnesium stearate and 2.6 parts by weight of hydroxypropylmethyl cellulose were well mixed together to give a uniform powdery mixture. This mixture was compressed into tablets by means of a commercially available tableting machine, and thus there were obtained such tablets each weighing about 200 mg and each containing 0.05 mg of the active ingredient.

Example 2 for Preparation 1.0 Parts by weight of Ro 20-1727, 55 parts by weight of lactose, 45 parts by weight of crystalline cellulose, 0.3 parts by weight of magnesium stearate and 2.6 parts by weight of hydroxypropylmethyl cellulose were well mixed together to give a uniform powdery mixture. This mixture was compressed into tablets by means of a commercially available tableting machine, and thus there were obtained such tablets each weighing about 200 mg and each containing 1.0 mg of the active ingredient.

INDUSTRIAL UTILIZABILITY OF THE INVENTION

According to this invention, there is provided as described hereinbefore a new pharmaceutical composition for therapeutic treatment or prevention of tardive dyskinesia, which is characterized in that the composition contains as the active ingredient such a compound having an enzyme-inhibitory activity against a phosphodiesterase. This pharmaceutical composition is useful and effective to suppress symptoms of tardive dyskinesia and can provide a new method for therapeutically treating or preventing tardive dyskinesia.

We claim:

1. A method for therapeutically treating tardive dyskinesia, which comprises administering a therapeutically effective amount of a compound which has an enzyme-inhibitory activity against a phosphodiesterase, and is able to penetrate the blood-brain barrier after administration of said compound, to a patient in need of the treatment and having received occurrence of tardive dyskinesia as induced by long-term administration of an antipsychotic drug which acts as an antagonist against the dopamine $D_2$ receptors in the dopamine neuron system in the brain.

2. The method according to claim 1 in which a therapeutically effective amount of a compound having an enzyme-inhibitory activity against phosphodiesterase IV and capable of penetrating the blood-brain barrier is administered.

3. The method according to claim 1 which a therapeutically effective amount of rollpram is administered.

4. The method according to claim 1 in which a therapeutically effective amount of 3-isobutyl-1-methylxanthine is administered.

5. The method according to claim 1 in which a therapeutically effective amount of Ro 20-1724 is administered.

* * * * *